(12) United States Patent
Fugetsu

(10) Patent No.: US 6,685,837 B2
(45) Date of Patent: Feb. 3, 2004

(54) METHOD FOR SEPARATING AND ANALYZING HYDROGEN ION AND ION CHROMATOGRAPHIC INSTRUMENT

(75) Inventor: Bunshi Fugetsu, Sapporo (JP)

(73) Assignee: Japan Science and Technology Corporation, Saitama (JP)

(*) Notice: Subject to any disclaimer, the term of this patent is extended or adjusted under 35 U.S.C. 154(b) by 0 days.

(21) Appl. No.: 10/311,927

(22) PCT Filed: Jun. 20, 2001

(86) PCT No.: PCT/JP01/05276

§ 371 (c)(1),
(2), (4) Date: Apr. 2, 2003

(87) PCT Pub. No.: WO01/98771

PCT Pub. Date: Dec. 27, 2001

(65) Prior Publication Data

US 2003/0146160 A1 Aug. 7, 2003

(30) Foreign Application Priority Data

Jun. 20, 2000 (JP) ......................................... 2000-185293

(51) Int. Cl.$^7$ .............................................. B01D 15/08
(52) U.S. Cl. .................... 210/656; 210/198.2; 95/82; 96/101
(58) Field of Search ................................. 210/635, 656, 210/198.2; 423/644, 648.1; 95/82; 96/101

(56) References Cited

U.S. PATENT DOCUMENTS

| 4,276,060 | A | * | 6/1981 | Aldridge | 95/88 |
| 4,732,581 | A | * | 3/1988 | Cheh et al. | 95/87 |
| 5,904,749 | A | * | 5/1999 | Chen et al. | 95/86 |
| 6,277,329 | B1 | * | 8/2001 | Evans | 422/80 |

OTHER PUBLICATIONS

De Borba, B.M. et al., *Anal. Chem.*, vol. 72, pp. 96–100, Jan. 2000.
Tanaka, K. et al., *Journal of Chromatography A*, vol. 671, pp. 239–248, (1994).

* cited by examiner

Primary Examiner—Ernest G. Therkorn
(74) Attorney, Agent, or Firm—Wenderoth, Lind & Ponack, L.L.P.

(57) ABSTRACT

A method for the separation of hydrogen ion, characterized in that a substance having a conjugate base ($A^-$) of an acid (HA) as a functional group is used as a stationary phase, and an electrolyte containing a cation having a larger ion exchanging force than that of hydrogen ion is used as an eluent. The method allows the selective separation of hydrogen ion and the quantitative analysis thereof with high precision.

6 Claims, 15 Drawing Sheets

METHOD FOR SEPARATING AND ANALYZING HYDROGEN ION AND ION CHROMATOGRAPHIC INSTRUMENT

REFERENCE TO RELATED APPLICATIONS

This application is a 371 of PCT/JP01/05276 filed Jun. 20,20011.

TECHNICAL FIELD

The present invention relates to a method of separating hydrogen ion, a method of analyzing hydrogen ion, and an ion chromatography apparatus. More specifically, the invention of the present application relates to a novel method of separating and analyzing hydrogen ion, for which selective separation and accurate quantification have been considered difficult; these methods enable the selective separation of hydrogen ion from sample aqueous solutions and the quantitative analysis of hydrogen ion by ion chromatography; the present invention also relates to an ion chromatography apparatus that enable such methods.

BACKGROUND ART

Hydrogen ion is believed to be the most fundamental and important substance in various fields such as life science. Namely, it is impossible to understand chemical reactions, chemical equilibrium, electric chemical phenomena of solution systems or life processes in organisms, without considering the presence and chemical phenomenon of hydrogen ion. However, even though hydrogen ion is a fundamental and important substance, separation of hydrogen ion has previously been considered very difficult.

On the other hand, as a method of quantifying and measuring hydrogen ion, pH titration and pH meter are widely used. However, in these methods, measurement with high sensitivity and high precision is considered difficult. Therefore, a novel quantification and measurement method that enables the measurement of hydrogen ion with high sensitivity and high precision has been desired.

The invention of the present application has been accomplished in view of the matters as described above, and its subject is to provide a novel method of separating hydrogen ion and a novel method of analyzing hydrogen ion that enables the selective separation of hydrogen ion from sample aqueous solutions and the quantitative analysis of the separated hydrogen ion with high sensitivity and high precision, as well as an ion chromatography apparatus for such methods.

DISCLOSURE OF THE INVENTION

In order to solve the above-mentioned subject, the invention of the present application firstly provides a method for separating hydrogen ion selectively by chromatography, which comprises using a substance with a functional group which is a conjugate base ($A^-$) of an acid (HA) as a stationary phase, and using an electrolyte which contains a cation that exhibits higher ion exchanging force than hydrogen as an eluent.

Secondly, the invention of the present application provides the method for separating hydrogen ion of claim 1, wherein the separation of trace amounts of hydrogen ion in an aqueous sample solution is enabled by pre-protonating the conjugate base ($A^-$), which is the functional group of the stationary phase.

Thirdly, the invention of the present application provides a method for analyzing hydrogen ion, which comprises quantitatively analyzing the hydrogen ion separated by the above methods, and fourthly, such method for analyzing hydrogen ion, wherein the hydrogen ion is quantitatively analyzed by electric conductivity measuring method or electrode detecting method.

Fifthly, the invention of the present application provides an ion chromatography apparatus that separates hydrogen ion selectively, which comprises a separation column stationary phase that contains a substance having a conjugate base ($A^-$) of an acid (HA) as a functional group, and an eluent that contains an electrolyte containing a cation that exhibits higher ion exchanging force than hydrogen; sixthly, the invention of the present application provides such ion chromatography apparatus, wherein part of the conjugate base ($A^-$), which is the functional group of the stationary phase, is pre-protonated (AH), thereby enabling the separation of trace amounts of hydrogen ion in an aqueous sample solution.

Further, seventhly, the invention of the present application provides the above ion chromatography apparatus, which further comprises an apparatus for the quantitative determination and analysis of the separated hydrogen ion; and eighthly, the invention of the present application provides the ion chromatography apparatus, wherein the apparatus for the quantitative determination and analysis is an electric conductivity measurement apparatus or an electrode detecting measurement apparatus.

BEST MODE FOR CARRYING OUT THE INVENTION

The invention of the present application has the characteristics as described above, and its embodiments are described hereinafter.

In the hydrogen ion separation method of the present invention, hydrogen ion is selectively separated from the sample aqueous solution by chromatography.

In this procedure, as the stationary phase of chromatograph, a substance having a conjugate base ($A^-$) of an acid (HA) is used. Here, as the conjugate base ($A^-$), any conjugate base which can receive hydrogen ion ($H^+$) can be used as the functional group of the separation column stationary phase. For example, a sulfonate group, carboxyl group, dodecylsulfate group, phosphate group and the like are exemplified. As an eluent, which acts as the mobile phase of the chromatograph, an aqueous electrolyte solution containing cation is used. The cation in this case should have ion exchanging force larger than that of hydrogen ion. As the cation, for example, a potassium ion, ammonium ion, sodium ion, lithium ion and the like are favorable.

Figure 1:
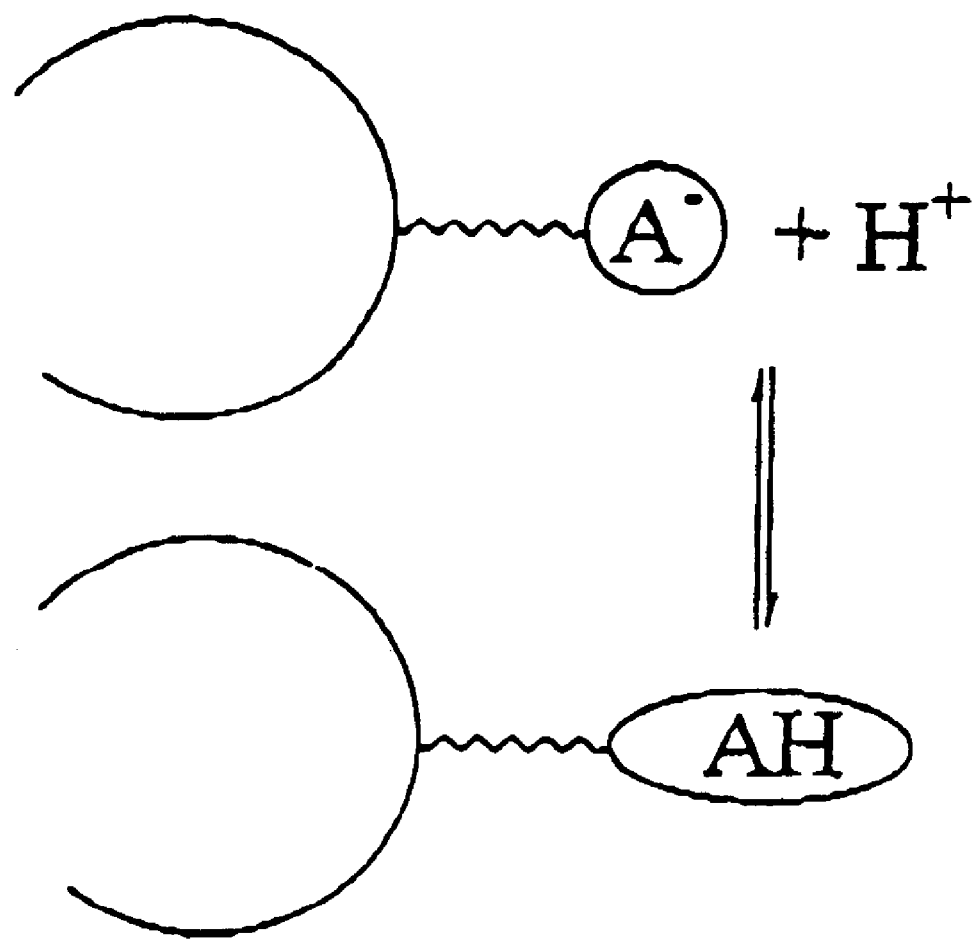
FIG. 1 illustrates the theory behind the method of the present invention.

FIG. 1 shows the theory behind the hydrogen ion separation method of the present invention.

By using a substance having a conjugate base ($A^-$) of an acid (HA) as the functional group for the stationary phase, hydrogen ion ($H^+$) protonates the conjugate base ($A^-$) of the acid, and produces a conjugate acid (HA). This property can be seen only by using hydrogen ion; hence, hydrogen ion can be separated selectively from other cations.

In the present method for hydrogen ion separation, the ion exchanging force of the cation contained in the eluent, which is an aqueous electrolyte solution, should be larger than the ion exchanging force of hydrogen ion. The reason for this is that since hydrogen ion shows, like other cations, an electrostatic interaction between the hydrogen ion and the conjugate base of an acid, hydrogen ion enhances the protonation of the conjugate base of an acid.

In the hydrogen ion separation method of the present invention, by adding a small amount of dodecylsulfate ion to the eluent, an electrolyte aqueous solution, di- or poly-valent cations can be prevented from being removed by the separation column. The reason for this is that by adding a small amount of dodecylsulfate ion, the di- or poly-valent cations are bonded to the dodecylsulfate ion, and converted into molecules having no charge.

In the invention of the present application, hydrogen ion separated by adsorption to the column stationary phase is eluted by the above-mentioned eluent; the hydrogen ion obtained can then be quantitatively analyzed by appropriate means. As the quantitative analysis, an electric conductivity method and other suitable detecting methods, for example, an electrode detection method and the like can be appropriately adopted. By using an electric conductivity method, direct detection and quantification is possible.

Regarding detection signals by an electric conductivity method, the equivalent ion conductivity is 349.8 for hydrogen ion, the equivalent ion conductivity is 73.5 when the ion in the eluent is a potassium ion, the equivalent ion conductivity is 38.7 for lithium ion, and the detection signal is in proportion to the difference in the electric conductivity; therefore, a calibration line can be provided.

Thus, according to the separation and analysis methods of the present invention, for example, correct and direct measurement of hydrogen ion which has not been realized by conventional pH titration methods and pH meter methods is made possible, and highly academic contributions as well as contributions to various fields such as industrial utility, medical care, life science, environment and the like can be expected. For example, acidic solutions of organic acids and inorganic acids for chemical industry, or gastric acid, acetic acid and the like relating to organisms and life, maybe subjected to the separation and analysis of the present invention. Further, separation and analysis of hydrogen ion in acid rain, and the like are also made possible.

Figure 2:
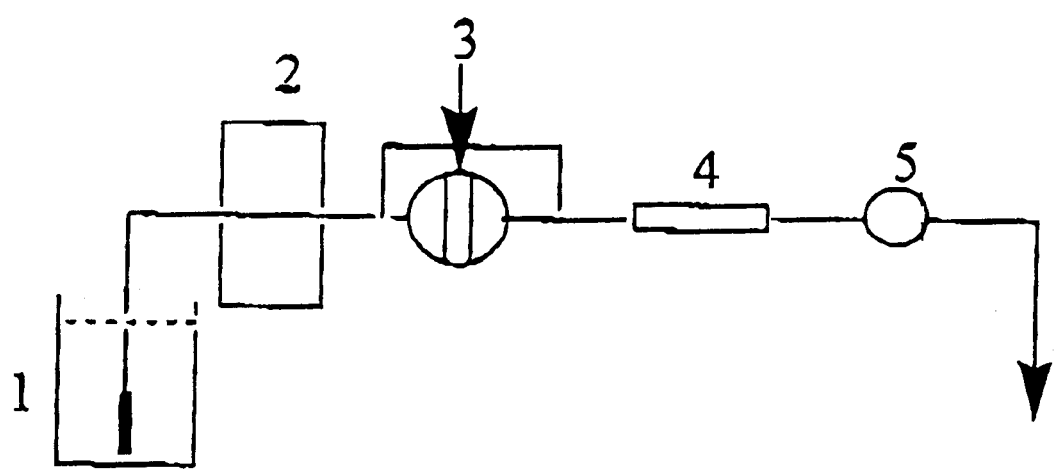
FIG. 2 shows an example of the structure of the ion chromatography apparatus of the present invention.

The invention of the present application provides an ion chromatography apparatus enabling separation and analysis of hydrogen ion having the above-described characteristics. One example of its structure is shown in FIG. 2.

An eluent storage tank (1), an apparatus for introducing an eluent into the separation column (2), a sample injection part (3), a hydrogen ion separation column (4), and a hydrogen ion detector (5) are connected. Here, in the hydrogen ion separation column (4), a substance having a conjugate base ($A^-$) of an acid (HA) as the functional group is used as the stationary phase as described above. The eluent contains cations as described above, and the hydrogen ion detector (5) is an electric conductivity measuring apparatus or the like.

The concentration of cation in the sample and the eluent is not particularly restricted. However, samples having extremely high salt concentration, for example, sea water and the like, may cause problems. In such a case, pre desalting is also effective. The flow ratio of the eluent is also not limited; for example, flow rates from 0.5 to 2.5 mL/min may be applied.

In another embodiment of the invention of the present application, by protonating (AH) a part of the conjugate base ($A^-$) that acts as the functional group in the stationary phase, separation of a trace amount of hydrogen ion in a sample aqueous solution is also made possible.

This is realized, specifically, by adding, for example, an acid such as 0.1 mM of nitric acid, to cause contact of the stationary phase with the mobile phase such as the eluent, to which a small amount of hydrogen ion has been added, thereby pre-protonating (AH) a part of the conjugate base ($A^-$) that acts as the functional group in the stationary phase.

Figure 3:
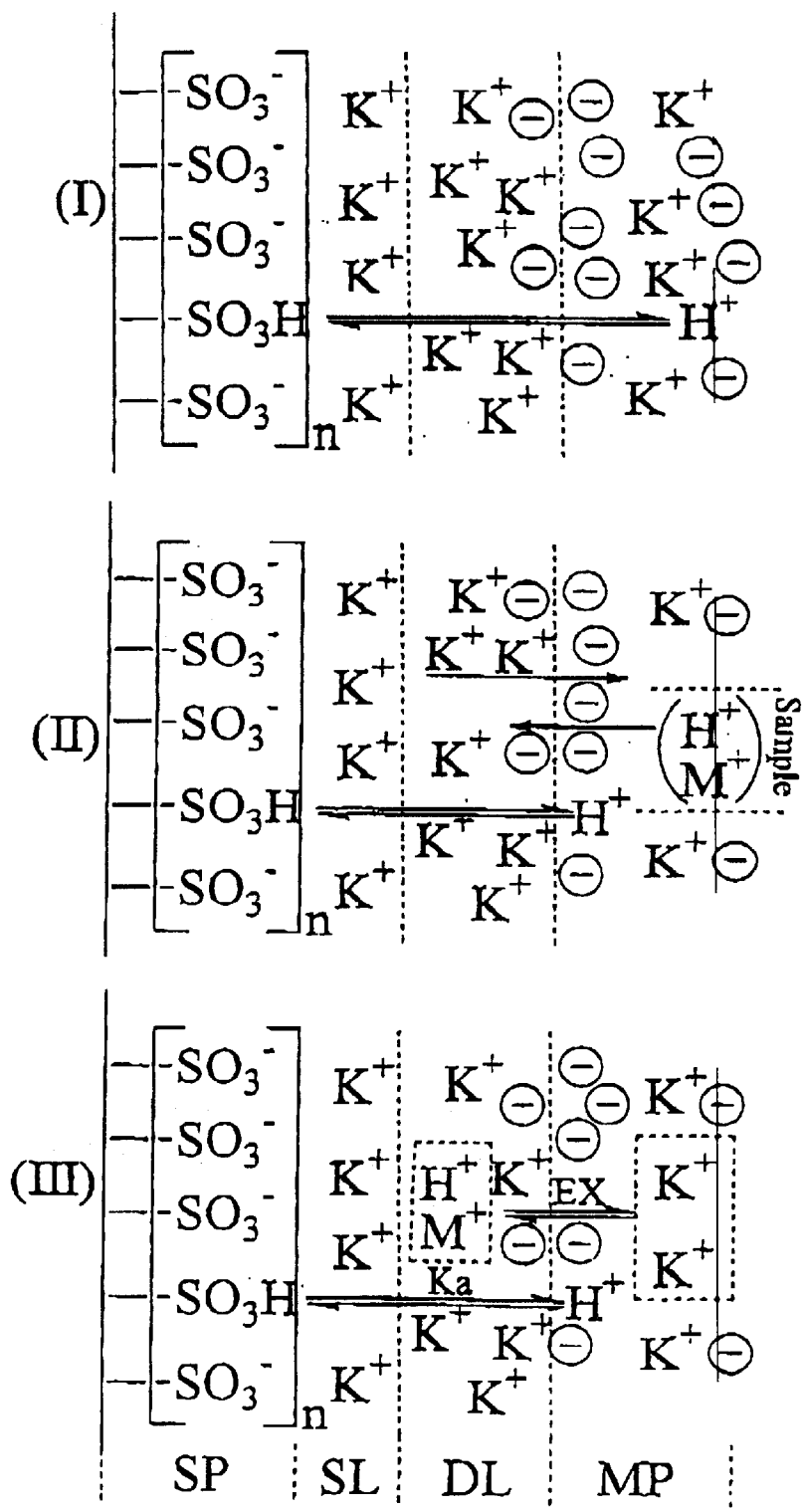
FIG. 3 illustrates the pre-protonation of the conjugate base of the stationary phase functional group.

For example, when the functional group is a sulfonate group ($-SO_3^-$) and nitric acid is added to a $KNO_3$ aqueous solution mobile phase to protonate part of the sulfonate group ($-SO_3^-$), the hydrogen ion separation may be explained theoretically as follows: By previously adding a small amount of hydrogen ion to the $KNO_3$ aqueous solution mobile phase using nitric acid, as shown in FIG. 3, a functional group ($R-SO_3^-$) in the stationary phase can be previously protonated. Since the hydrogen ion remaining (existing in the mobile phase) after protonation of the stationary phase is present only in very small amounts, compared to the exchanging ion (namely, mobile phase ion, for example, $K^+$), this hydrogen ion does not contribute to the construction of an ion exchanging field, or an electric bilayer. In other words, the electric bilayer, in this case, is constituted only of the exchanging ion, $K^+$ (Step (I)). When a sample aqueous solution containing hydrogen ion is injected into the separation column having such partially protonated stationary phase, the ion exchange between the hydrogen ion and the other cations (represented by $M^+$) with $K^+$ in the electric bilayer occur, and are kept and separated by the electric bilayer, namely, the stationary phase (Step (II)). Hydrogen ions (and other sample cations $M^+$) kept in the electric bilayer are again substituted by the mobile phase ion, $K^+$, and return to the mobile phase (Step (III)). For substituting N mol of hydrogen ion, N mol (equivalent) of the mobile phase ion is necessary.

Therefore, change in the electric conductivity of the mobile phase by ion exchange that occur between a mobile ion and a sample ion, namely, change in the strength of the detection signal, can be represented by the following formula:

$$\text{Conductance} = C_i(\lambda_i - \lambda_e)$$

wherein, $C_i$ represents the molar concentration of ion i in a sample, $\lambda_i$ represents the equivalent ion conductivity of ion i, and $\lambda_e$ represents the equivalent ion conductivity of a mobile phase ion. The equivalent ion conductivity of hydrogen ion is 349.8, and the equivalent ion conductivity of potassium ion is 73.5 (25° C.); therefore, the above-mentioned formula is shown as described below.

$$\text{Conductance} = 276.3\, C_i$$

Therefore, in a range from neutral to acidic, even hydrogen ion (sample ion) of lower concentration imparts a positive electric conductive signal to the detector.

The following examples are provided to illustrate the invention of the present application in further detail.

EXAMPLES

Example 1

In an apparatus structured as shown in FIG. 2, a commercially available cation exchange column for cardel was used as the separation column, with $-SO_3^-$ as the conjugate base $A^-$ used as the stationary phase functional group; the internal diameter was 4.6 mm and the length was 35 mm.

Figure 4:
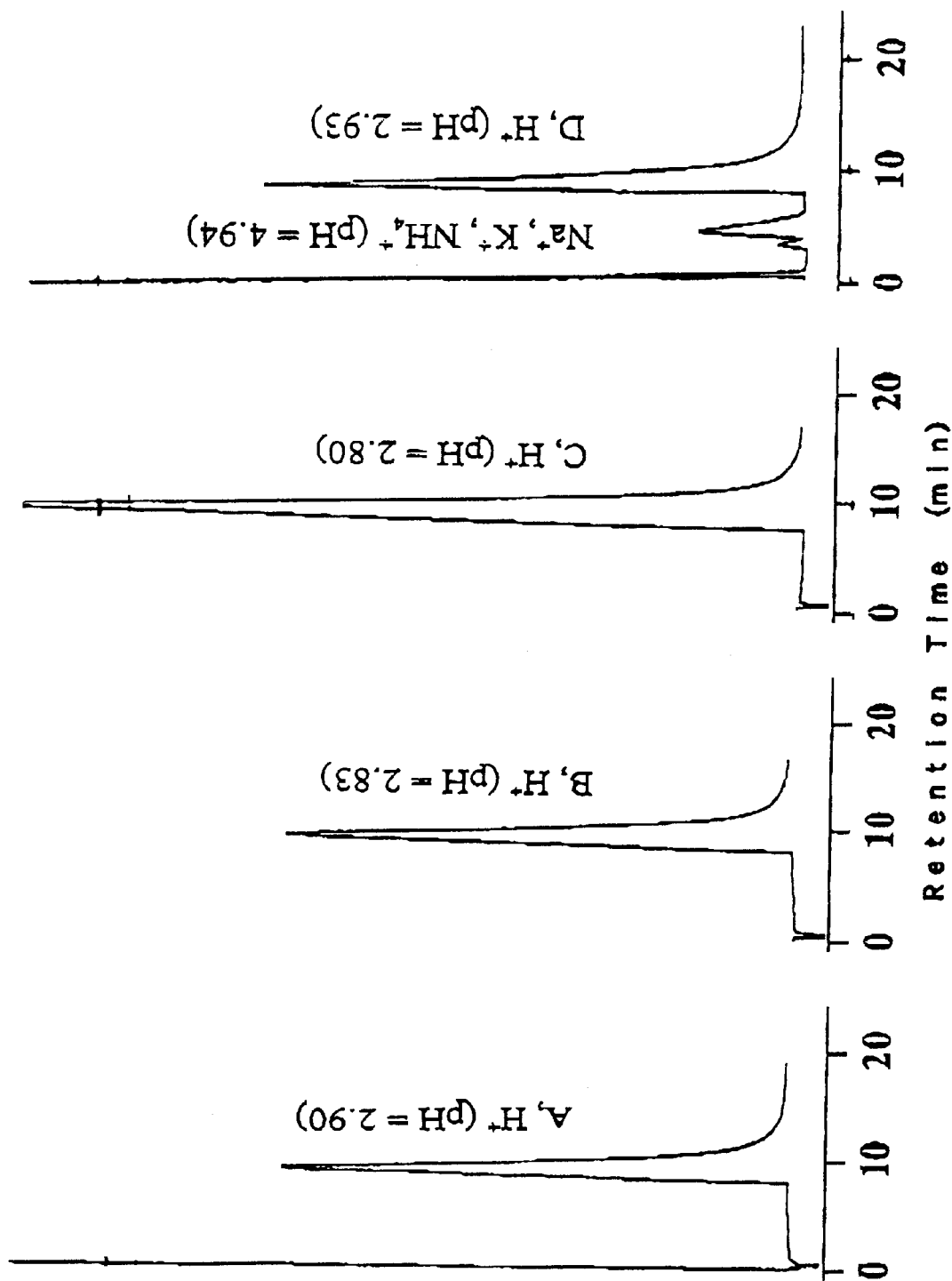
FIG. 4 shows the results for mixing aqueous lithium nitrate solution eluent and the separation of hydrogen ion.

The separation result of hydrogen ions, using 30 mM of aqueous lithium nitrate solution as the eluent, is shown in FIG. 4. A, B, C and D represent the following samples. A: 10.0 mM $H_2SO_4$, B: 20.0 mM $HClO_4$, C: 30.0 mM $H_3PO_4$, D: 10.0 mM for NaCl, $NH_4Cl$, KCl and $H_2SO_4$ respectively. The eluent was separated, and its pH was measured using a pH meter. The pH values shown in parentheses in FIG. 4 are the measured values. The eluent flow rate was 1.0 mL/min, and an electric conductivity meter was used as a detector.

Figure 5:
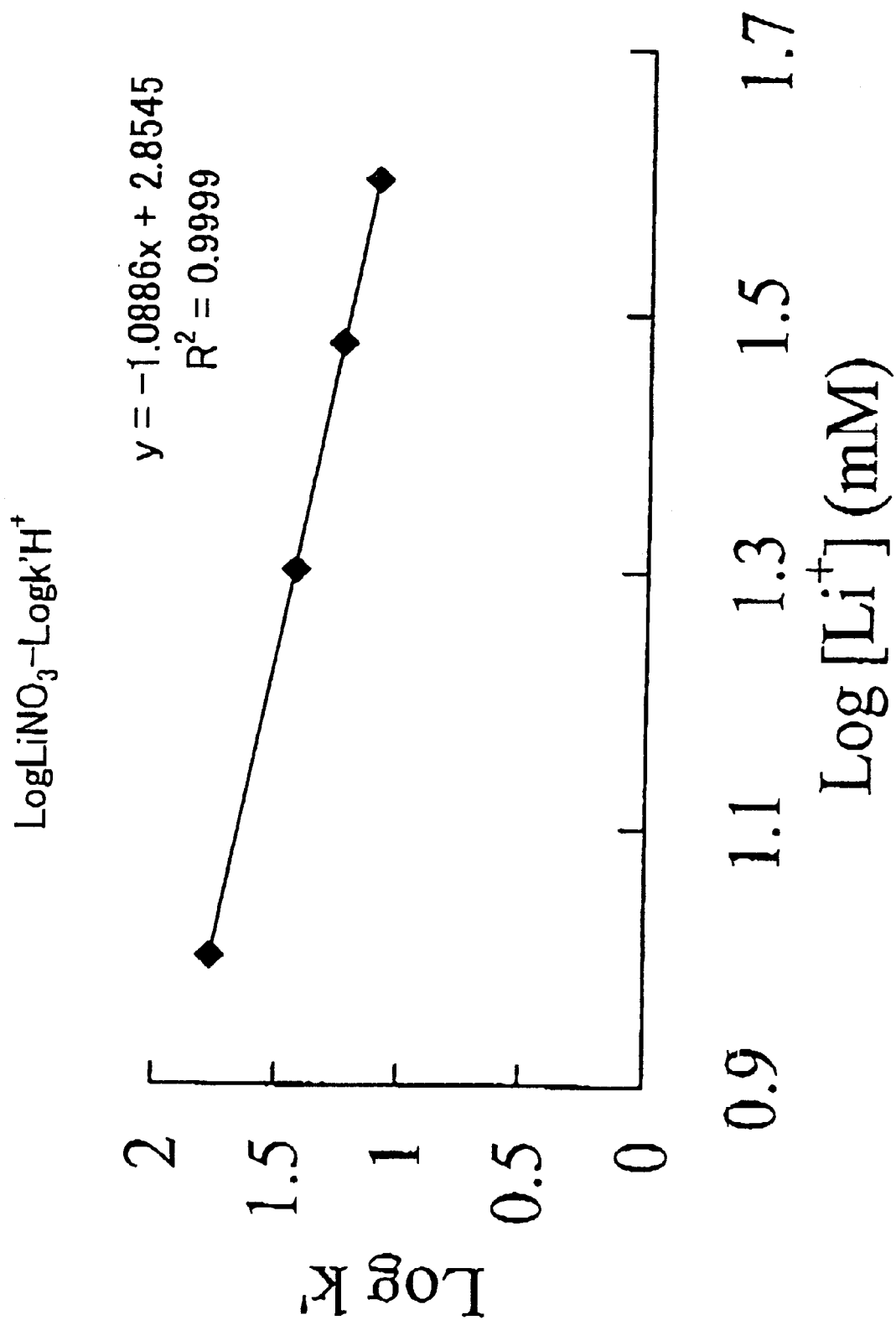
FIG. 5 shows the relation between the elution time of hydrogen ion and the concentration of lithium ion for the case shown in FIG. 4.
Figure 6:
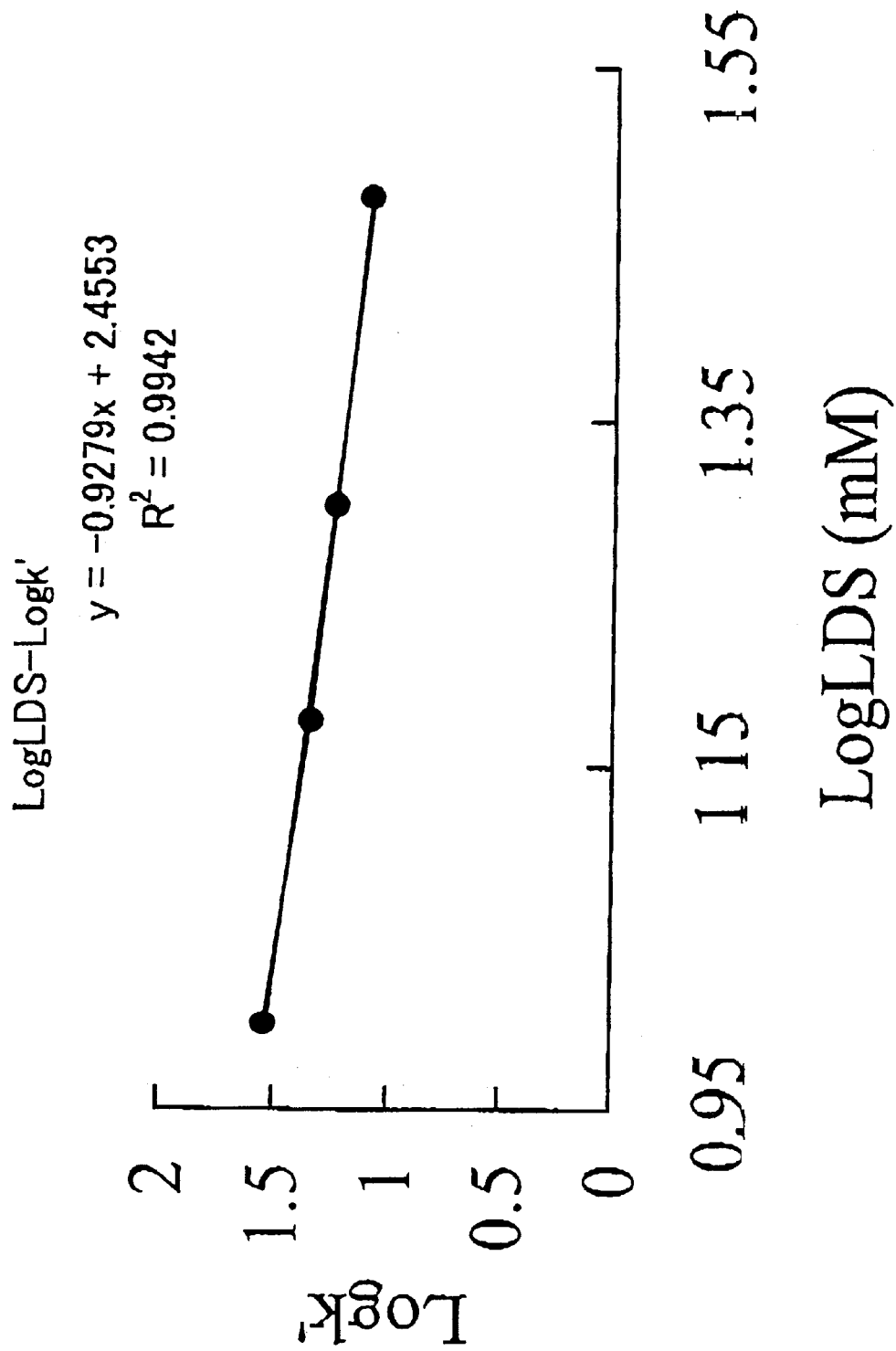
FIG. 6 shows the relation between the elution time of hydrogen ion and the concentration of lithium ion when an aqueous lithium dodecylsulfate solution was used as an eluent.

FIG. 5 shows the relation between the elution time of hydrogen ions and the concentration of lithium ions when aqueous lithium nitrate solution is used as an eluent; in FIG. 5, k' represents the retention constant of hydrogen ion in the column. FIG. 6 shows the relation between the elution time of hydrogen ion and the concentration of lithium ion when aqueous lithium dodecylsulfate solution is used as an eluent; k' in the figure represents the retention constant of hydrogen ion in the column.

Example 2

Figure 7:
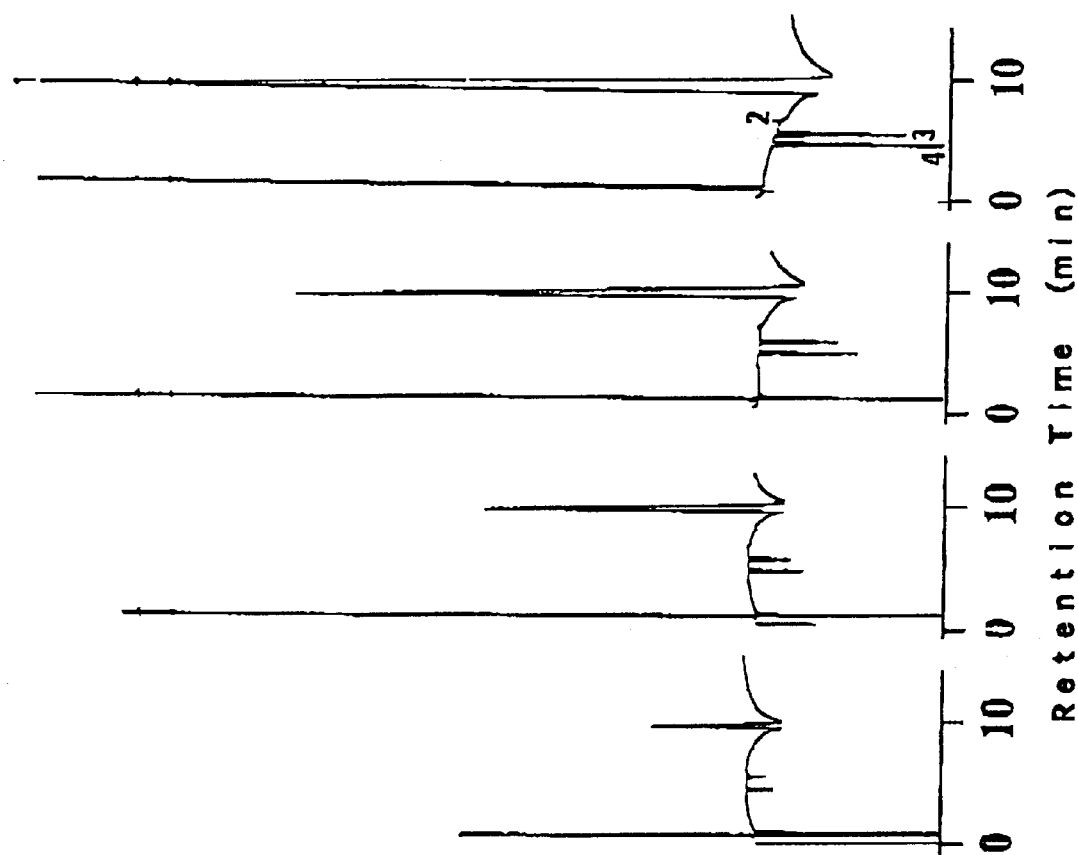
FIG. 7 shows the result of the separation of hydrogen ion when an aqueous $KNO_3$ solution was used as an eluent.

In an apparatus structured as shown in FIG. 2, separation of hydrogen ion was conducted using 40.0 mM of aqueous $KNO_3$ solution as an eluent. The column used was obtained by modifying a commercially available ODS-packed column with lithium dodecylsulfate micelle. The internal diameter was 4.6 mm and the length was 150 mm. The flow rate of the eluent mobile phase was 2.0 mL/min, and an electric conductivity meter was used as a detector. The cation concentrations in the sample were 1.0, 2.5, 5.0 and 10.0 mM for $Li^+$, $Na^+$, $NH_4^+$ and $H^+$, respectively. The results of this separation are shown in FIG. 7. Peaks in the figure indicate the following: $1=H^+$, $2=NH_4^+$, $3=Na^+$, $4=Li^+$.

The elution order was as follows: $Li^+>Na+>NH_4^+>H^+$, indicating that hydrogen ion ($H^+$) is retained most. Such extremely high selectivity for hydrogen ion ($H^+$) has never been realized by ion exchange chromatography that uses conventional ion exchange separation theory.

Example 3

Figure 8:
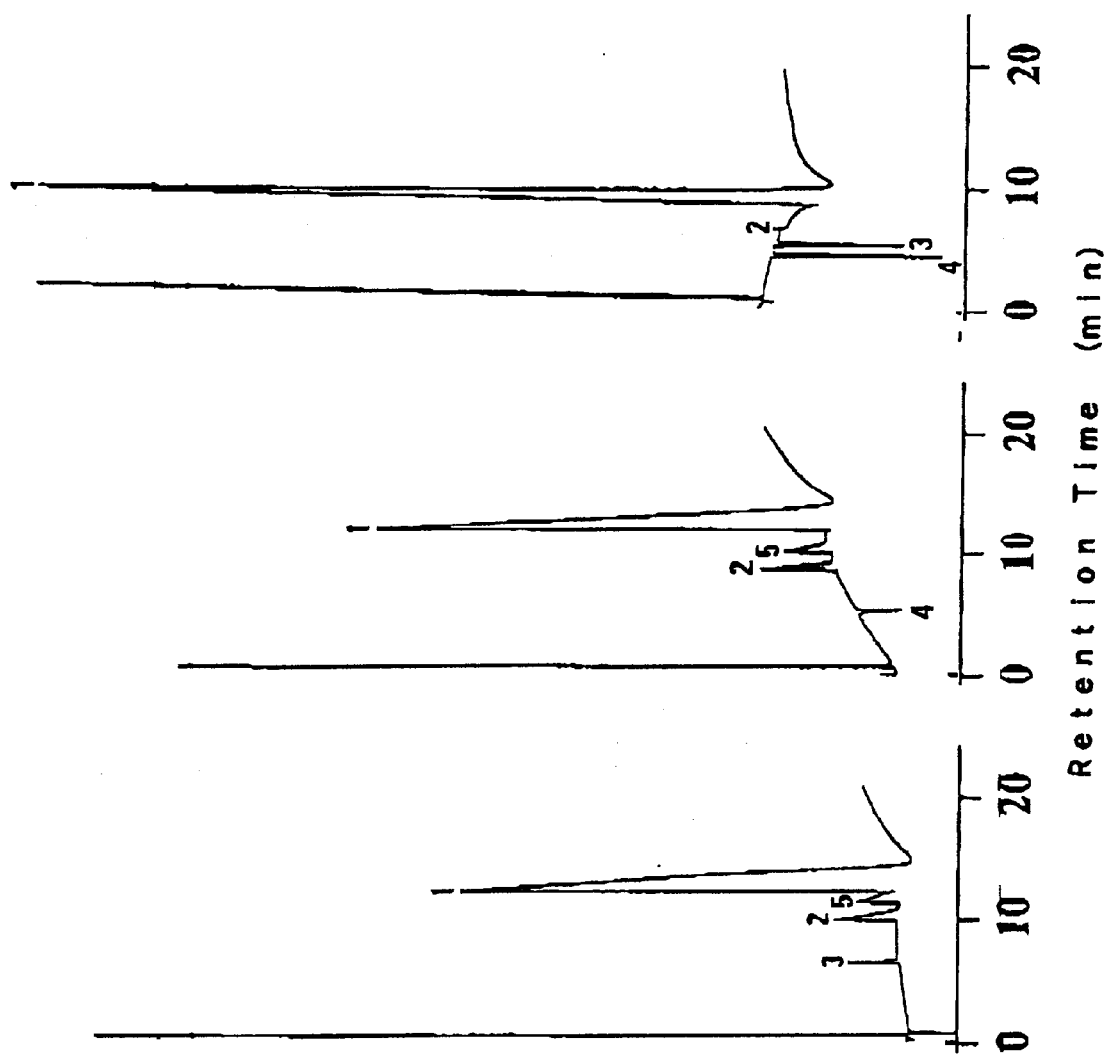
FIG. 8 shows the result of the separation of hydrogen ion when $LiNO_3$, $NaNO_3$ and $KNO_3$ were each used as an eluent.

FIG. 8 shows the results of the same hydrogen ion separation as described in Example 2, using 60.0 mM $LiNO_3$ (left), 40.0 mM $NaNO_3$ (center) and 40.0 mM $KON_3$ (right) as the eluent mobile phase. The cation concentrations in the samples were 10.0 mM for $Li^+$, $Na^+$, $NH_4^+$, $K^+$ and $H^+$, respectively. Peaks in the figure indicate the following: $1=H^+$, $2=NH_4^+$, $3=Na^+$, $4=Li^+$, $5=K^+$.

The elution order was as follows; $Li^+>Na^+>NH_4^+K^+>H^+$, indicating that hydrogen ion ($H^+$) is retained most. Such extremely high selectivity for hydrogen ion ($H^+$) has never been realized by ion exchange chromatography that uses conventional ion exchange separation theory.

Example 4

Figure 9:
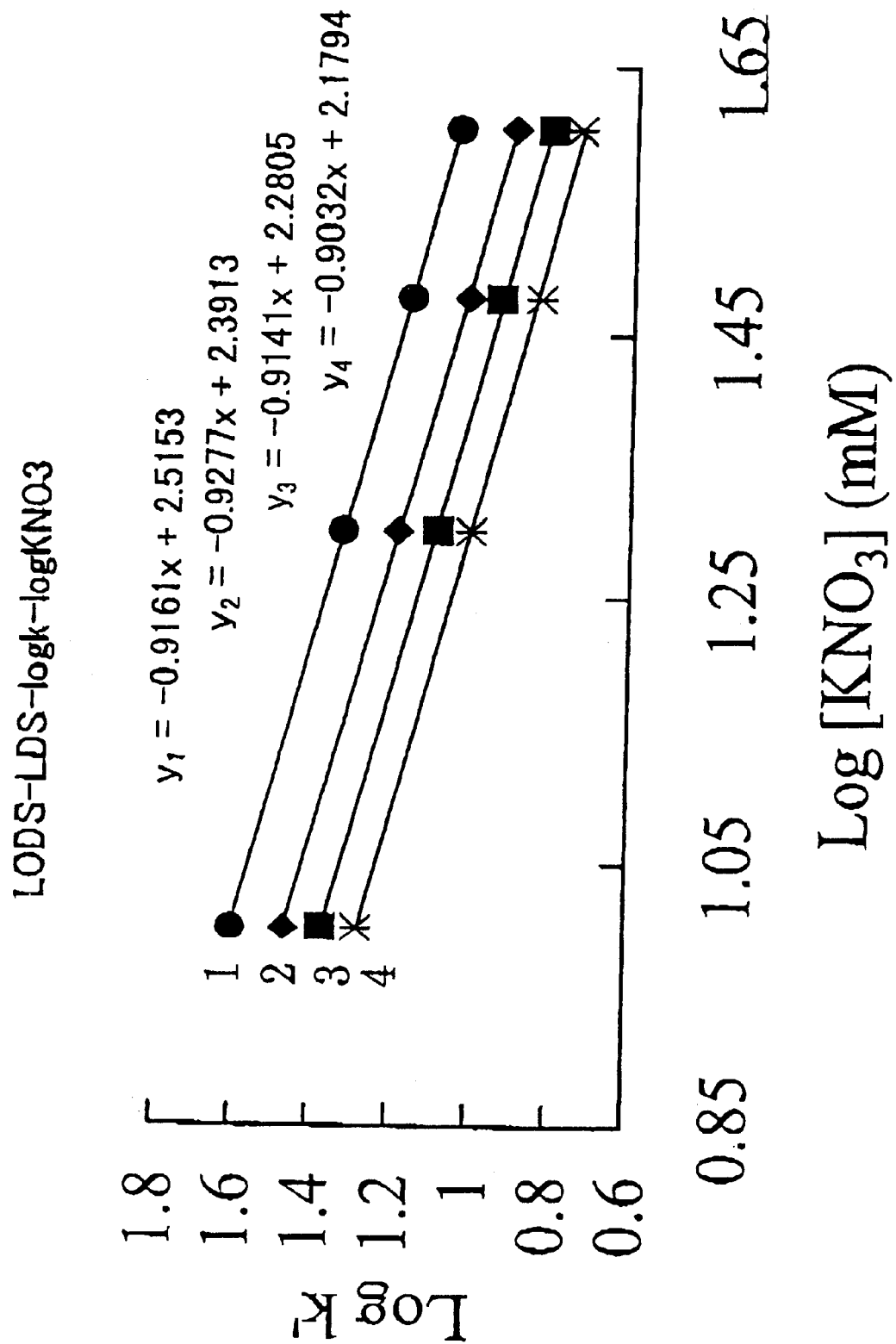
FIG. 9 is shows the relation between the elution time of the analysis subject ion and the concentration of $KNO_3$ when an aqueous potassium nitrate solution was used as an eluent.

In the same manner as described in Example 2, the relation between the elution time of a subject ion and the $KNO_3$ concentration was evaluated, using aqueous potassium nitrate solution as the eluent mobile phase. Results are shown in FIG. 9; k' in the figure indicates the capacity factor.

Figure 10:
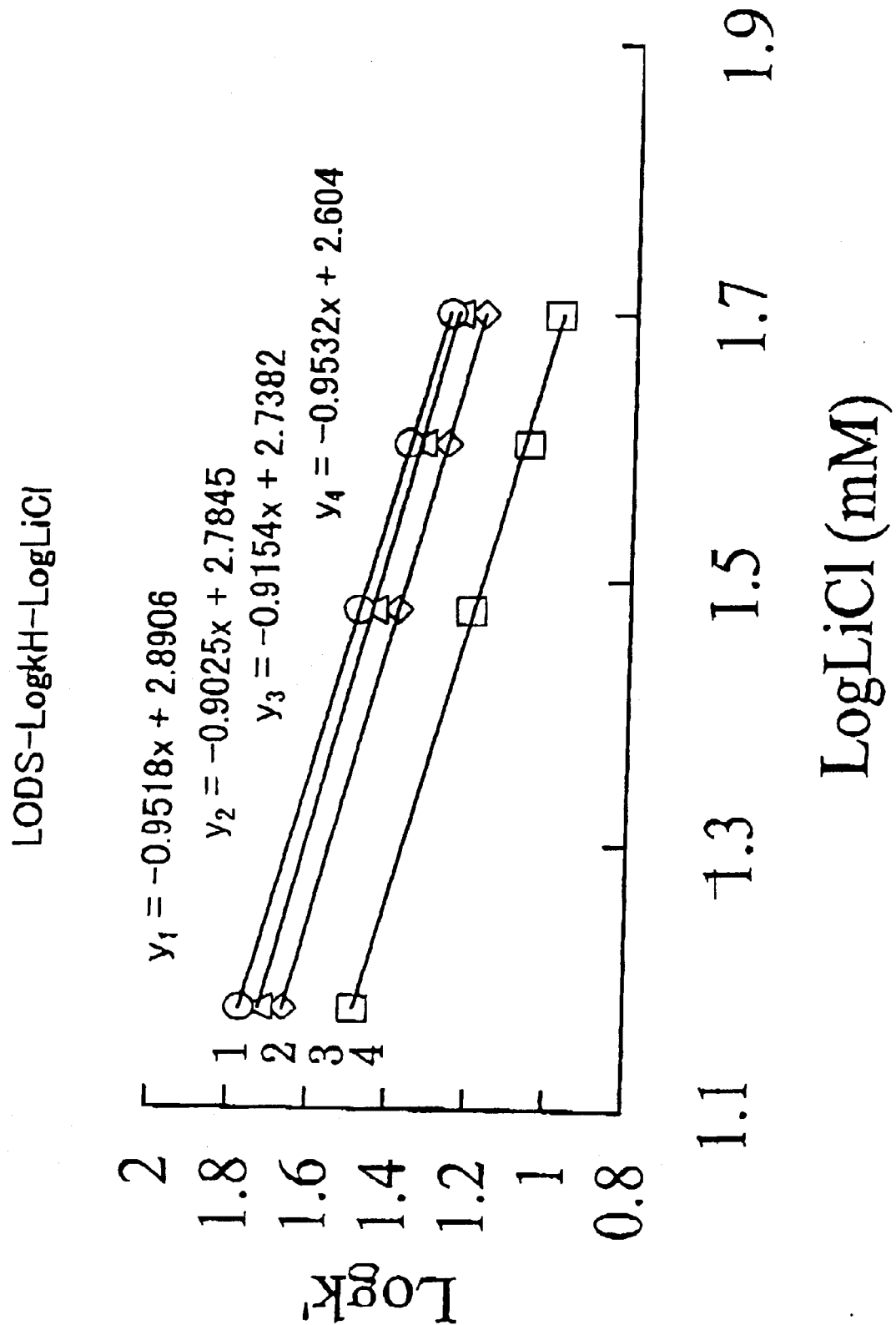
FIG. 10 shows the relation between the elution time of the analysis subject ion and the concentration of LiCl when aqueous lithium hydrochloride solution was used as an eluent.
Figure 11:
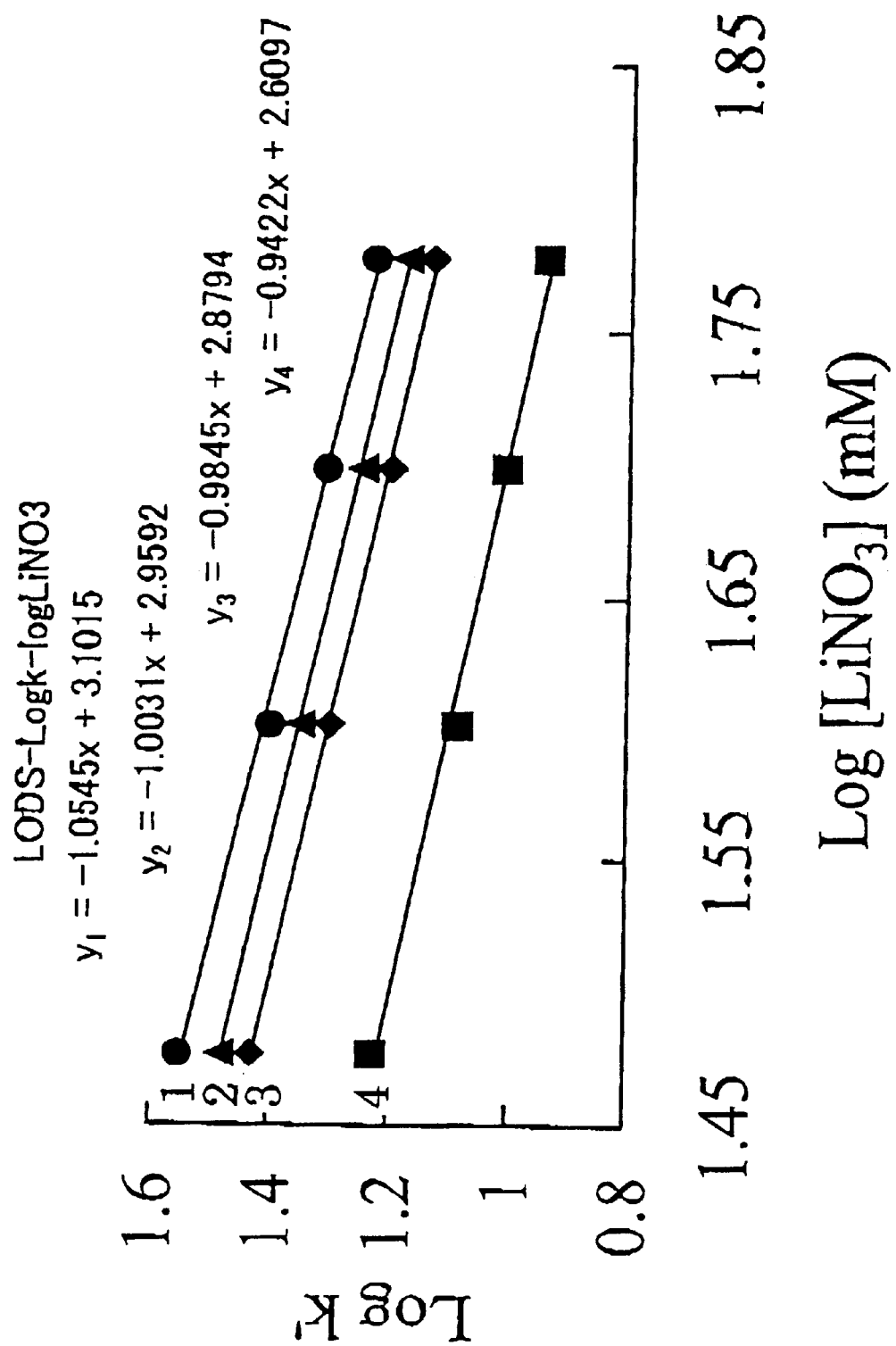
FIG. 11 shows the relation between the elution time of the analysis subject ion and the concentration of $LiNO_4$ when aqueous lithium nitrate solution was used as an eluent.
Figure 12:
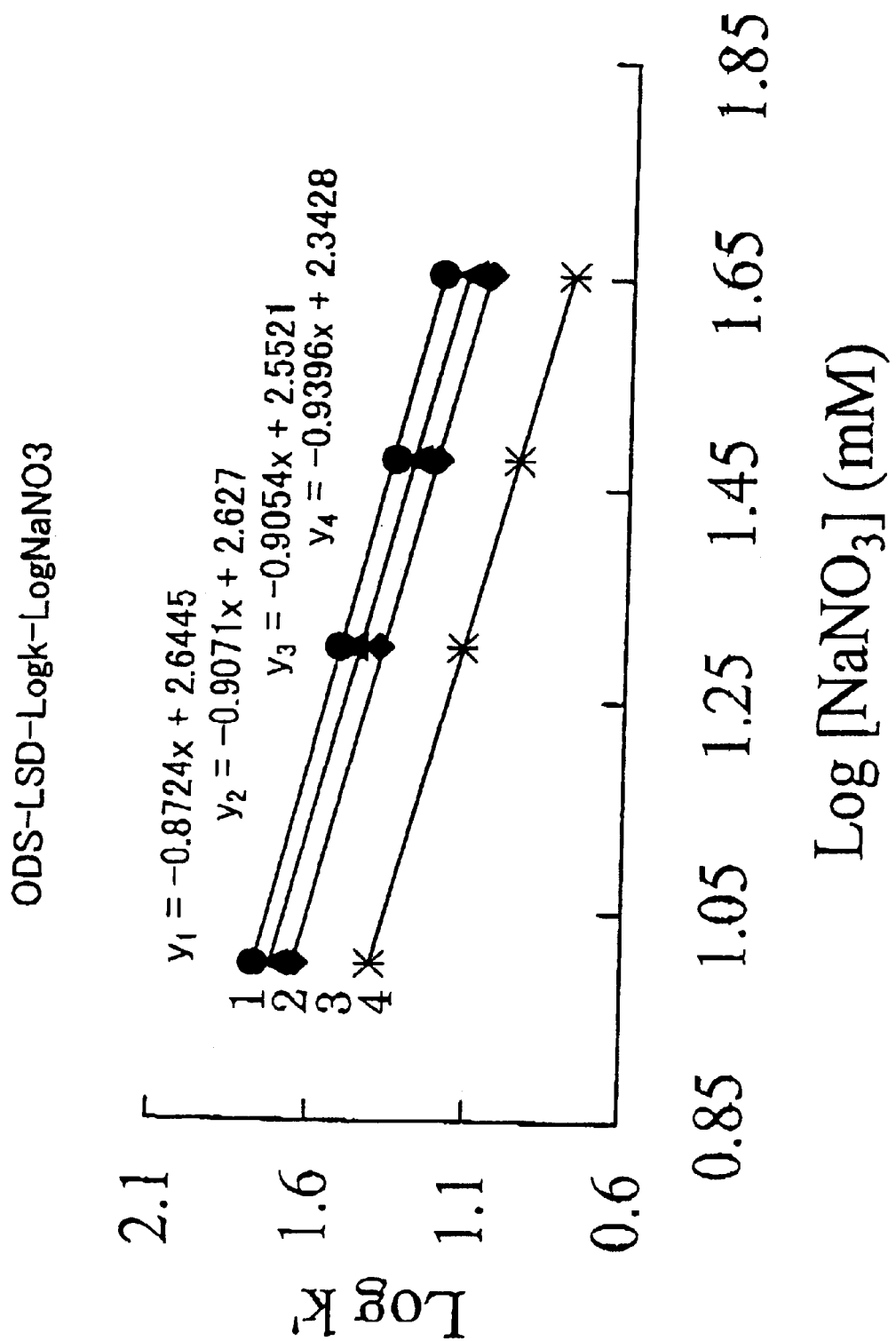
FIG. 12 shows the relation between the elution time of the analysis subject ion and the concentration of $NaNO_3$ when aqueous sodium nitrate solution was used as an eluent.

FIG. 10 shows the results when aqueous lithium hydrochloride solution is used; FIG. 11 shows the results when aqueous lithium nitrate solution was used; and FIG. 12 shows the results when aqueous sodium nitrate solution was used.

Example 5

Figure 13:
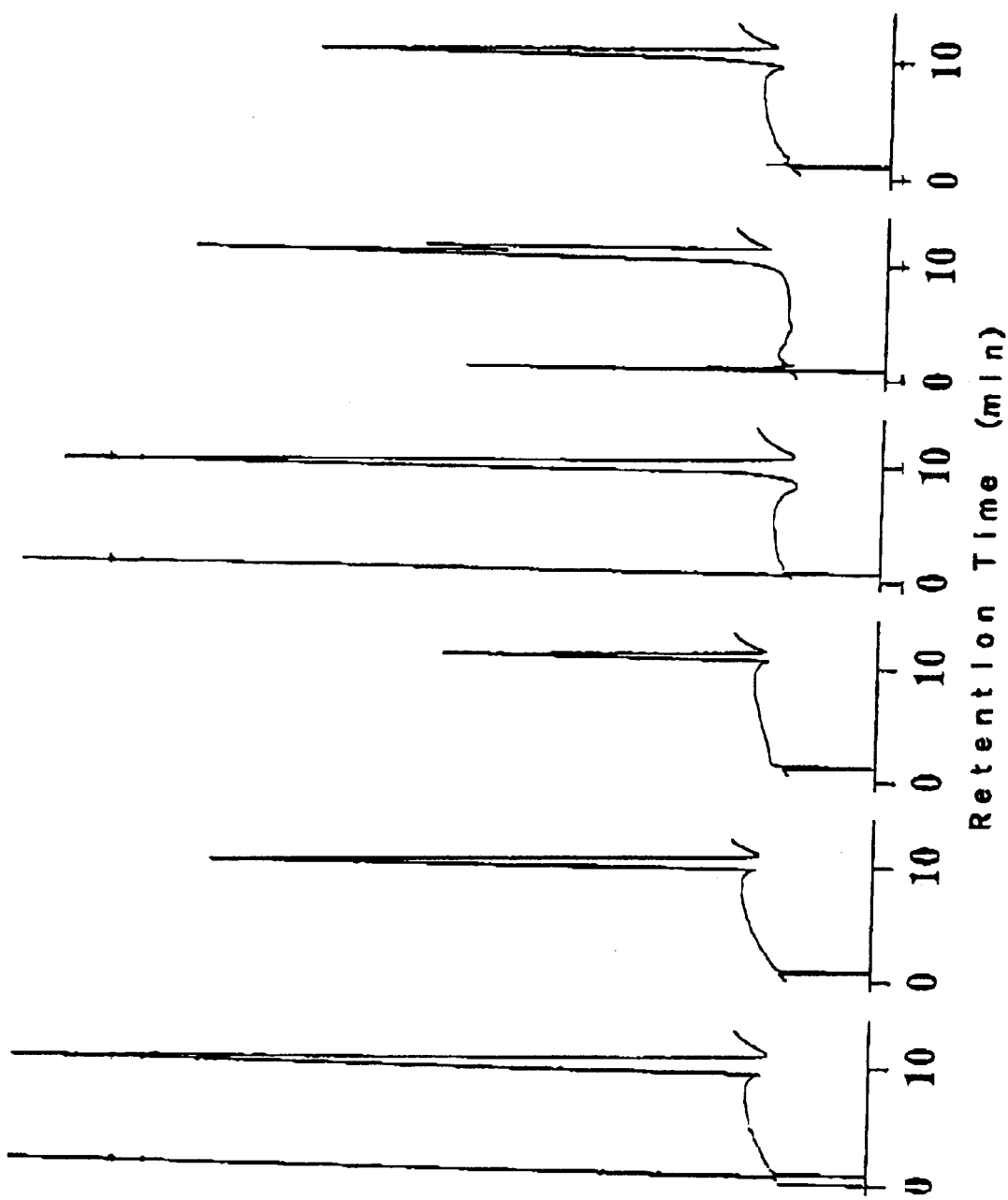
FIG. 13 shows the results of the separation of hydrogen ion in sulfuric acid ($1^{st}$), perchlorate ($2^{nd}$), phosphoric acid ($3^{rd}$), L-ascorbic acid ($4^{th}$), tartaric acid ($5^{th}$) and phthalic acid ($6^{th}$) (from left to right).

FIG. 13 shows the results of separation of hydrogen ion in sulfuric acid ($1^{st}$), perchlorate ($2^{nd}$), phosphoric acid ($3^{rd}$), L-ascorbic acid ($4^{th}$), tartaric acid ($5^{th}$) and phthalic acid ($6^{th}$), (from left to right) samples. The concentrations of the acids are each 10.0 mM, and other conditions are the same as described in Example 2.

In all cases, excellent separation of hydrogen ion ($H^+$) was observed.

Example 6

According to the basic theory shown in FIG. 3, separation and analysis of a trace amount of hydrogen ion were conducted by protonating the functional group, or the conjugate base in the stationary phase.

Figure 14:
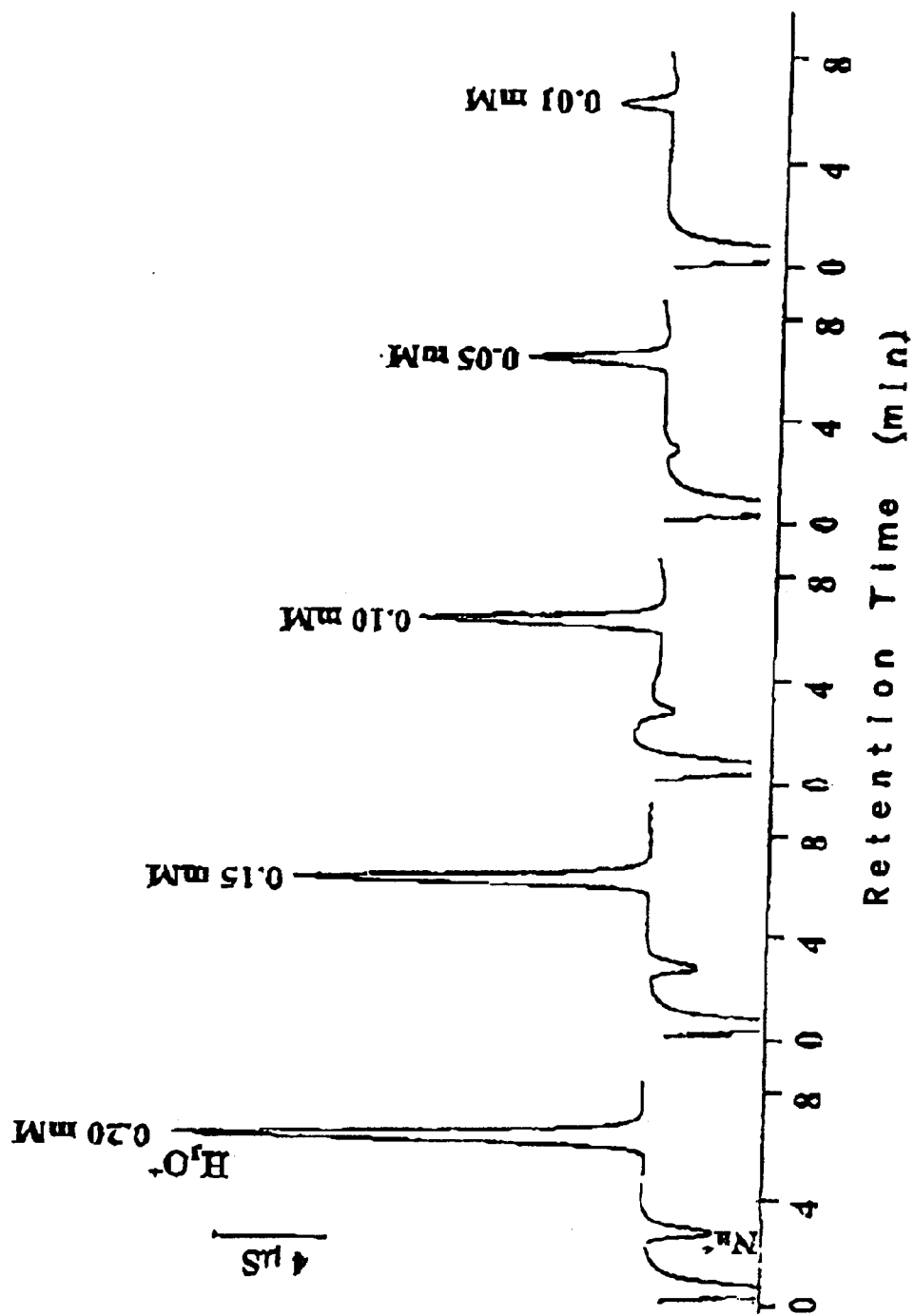
FIG. 14 shows the result of Example 6 in which the conjugate base of the stationary phase functional group was previously protonated.

A commercially available strong acid type cation exchange column (35×4.6 mm, i.d.) was used as a separation column, and an aqueous solution of 20 mM $KNO_3+HNO_3$ (pH: 3.80) to which hydrogen ion had been previously added was used as the mobile phase, and this was used also as the eluent. The flow rate of the mobile phase was 1.0 mL/min., and a mixed aqueous solution of NaCl and HCl was used. FIG. 14 indicates the results of separation of hydrogen ion, and shows the results when the (each) concentration of $Na^+$ and $H^+$ was 0.01 mM ($1^{st}$), 0.05 mM ($2^{nd}$), 0.10 mM ($3^{rd}$), 0.15 mM ($4^{th}$) and 0.20 mM ($5^{th}$), from right to left in the figure. The sample injection amount was 100 μL, and the detector was based on electric conductivity.

Example 7

Separation and analysis of a trace amount of hydrogen ion were conducted in the same manner as described in Example 6.

The column used was obtained by modifying an ODS-packed column with dodecylsulfate micelle (250×4.6 mm, i.d.). An aqueous solution of 40 mM $KNO_3+HNO_3$ (pH: 3.80) to which hydrogen ion had been previously added was used as the mobile phase, and this was used also as an eluent. The flow rate was 1.0 mL/min., and a mixed aqueous solution of 1.0 mM $Li^+$, $Na^+$ and $H^+$ was used as a sample. The sample injection amount was 100 μL, and the detector was based on electric conductivity.

Figure 15:
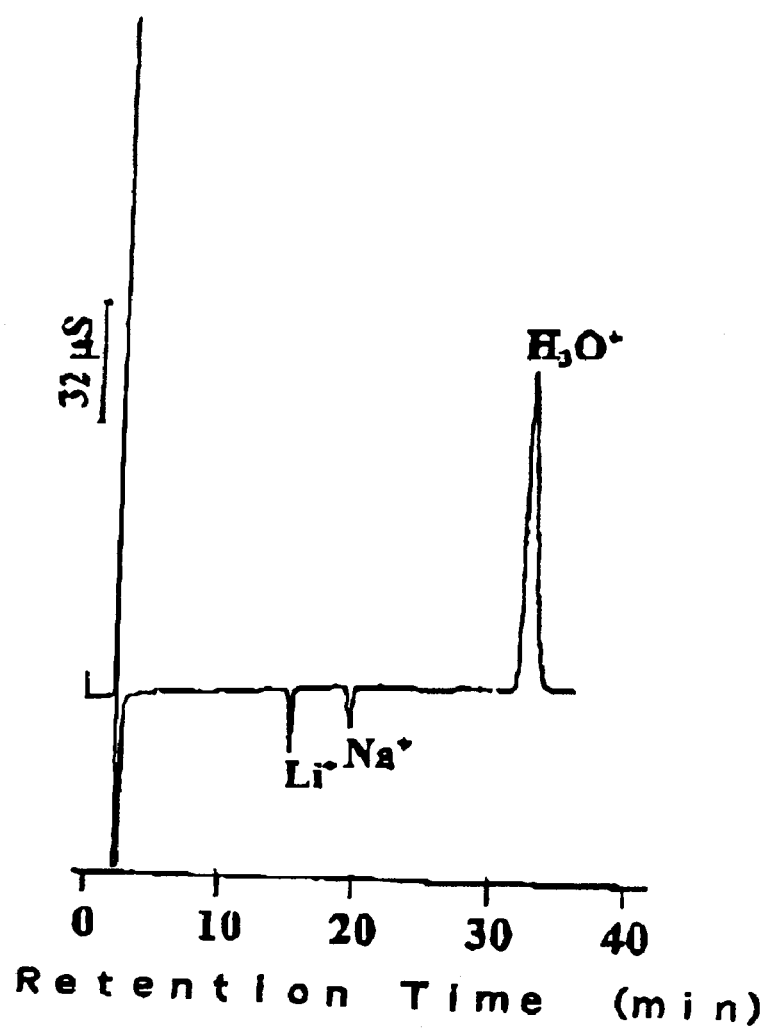
FIG. 15 shows the result of Example 7, different from that shown in FIG. 14.

FIG. 15 shows the results of separation of hydrogen ion.

Industrial Applicability

As described in detail above, according to the invention of the present application, selective separation of hydrogen ion and quantitative analysis of hydrogen ion at high accuracy that were previously difficult are made possible. Academic contribution as well as contributions to various fields such as industrial utility, medical care, life science, environment and the like, are expected.

What is claimed is:

1. A method for separating hydrogen ion selectively by chromatography, which comprises in a substance with a functional group which is a conjugate base ($A^-$) of an acid (HA), pre-protonating the conjugate base ($A^-$) and using this substance as a stationary phase, and using an electrolyte which contains a cation that exhibits higher ion exchanging force than hydrogen as an eluent.

2. A method for analyzing hydrogen ion, which comprises quantitatively analyzing the hydrogen ion separated by the method of claim 1.

3. The method for analyzing hydrogen ion of claim 2, wherein the hydrogen ion is quantitatively analyzed by electric conductivity measuring method or electrode detecting method.

4. An ion chromatography apparatus that separates hydrogen ion selectively, which comprises a separation column stationary phase that contains a substance with a functional group which is a conjugate base ($A^-$) of an acid (HA), for which the conjugate base ($A^-$) is pre-protonating and an eluent that contains an electrolyte containing a cation that exhibits higher ion exchanging force than hydrogen.

5. The ion chromatography apparatus of claim 4, which further comprises an apparatus for the quantitative determination and analysis of the separated hydrogen ion.

6. The ion chromatography apparatus of claim 5, wherein the apparatus for the quantitative determination and analysis is an electric conductivity measurement apparatus or an electrode detecting measurement apparatus.

* * * * *